United States Patent
Chen et al.

(10) Patent No.: US 10,188,685 B2
(45) Date of Patent: Jan. 29, 2019

(54) **USE OF *LACTOBACILLUS PLANTARUM* COMPOSITION FOR MANUFACTURING ANTI-FATIGUE PROBIOTIC COMPOSITION TO IMPROVE EXERCISE PERFORMANCE**

(71) Applicant: NATIONAL TAIWAN SPORT UNIVERSITY, Taoyuan (TW)

(72) Inventors: Yi-Ming Chen, Taoyuan (TW); Tsung-Yu Tsai, Taoyuan (TW); Chi-Chang Huang, Taoyuan (TW)

(73) Assignees: NATIONAL TAIWAN SPORT UNIVERSITY, Taoyuan (TW); SYNBIO TECH INC., Kaohsiung (TW)

( * ) Notice: Subject to any disclaimer, the term of this patent is extended or adjusted under 35 U.S.C. 154(b) by 0 days.

(21) Appl. No.: 15/385,786

(22) Filed: Dec. 20, 2016

(65) Prior Publication Data
US 2018/0055893 A1 Mar. 1, 2018

(30) Foreign Application Priority Data
Aug. 24, 2016 (TW) .............................. 105126982 A (51) Int. Cl.
| | | |
|---|---|---|
| *A61K 35/747* | (2015.01) | |
| *A23K 20/10* | (2016.01) | |
| *A23L 33/135* | (2016.01) | |
| *A23L 2/52* | (2006.01) | |
| *A61K 35/65* | (2015.01) | |
| *A61K 36/064* | (2006.01) | |
| *A61K 36/48* | (2006.01) | |
| *A61K 35/00* | (2006.01) | |

(52) U.S. Cl.
CPC ............ *A61K 35/747* (2013.01); *A23K 20/10* (2016.05); *A23L 2/52* (2013.01); *A23L 33/135* (2016.08); *A61K 35/65* (2013.01); *A61K 36/064* (2013.01); *A61K 36/48* (2013.01); *A23V 2002/00* (2013.01); *A23V 2200/33* (2013.01); *A61K 2035/115* (2013.01)

(58) Field of Classification Search
None
See application file for complete search history.

(56) References Cited

U.S. PATENT DOCUMENTS

| | | |
|---|---|---|
| 2008/0312474 A1 | 12/2008 | Liu et al. |
| 2010/0048695 A1 | 2/2010 | Ono et al. |
| 2010/0168040 A1 | 7/2010 | Komatsu et al. |
| 2012/0077873 A1 | 3/2012 | Zachwieja et al. |
| 2014/0017217 A1 | 1/2014 | Tsubouchi et al. |
| 2015/0018292 A1 | 1/2015 | Sloth Weidner et al. |

FOREIGN PATENT DOCUMENTS

| | | |
|---|---|---|
| TW | 200848068 | 12/2008 |
| TW | 200904406 | 2/2009 |
| TW | 201244647 | 11/2012 |

OTHER PUBLICATIONS

Chen et al. "Lactobacillus plantarum TWK10 supplementation improves exercise performance and increases muscle mass in mice". Nutrients 2016, 8, 205, pp. 1-15; Published: Apr. 7, 2016.*
Appukutty et al. "Effect of orally administered soy milk fermented with Lactobacillus plantarum LAB12 and physical exercise on murine immune responses". Benef. Microbes. 2015, 6 (4), pp. 491-496; (epub Apr. 22, 2015).*
Sullivan et al. "Effect of supplement with lactic-acid producing bacteria on fatigue and physical activity in patients with chronic fatigue syndrome". Nutrition Journal 2009, 8:4, pp. 1-6.*
Report from China General Microbiological Culture Collection Center Issued on Sep. 26, 2016 with English translation.
Report from The Food Industry Research and Development Institute, Issued on Jul. 11, 2016 with English Translation.
Chen et al. "Lactobacillus plantrum TWK10 supplementation improves exercise performance and increases muscle mass in mice". Nutrients 2016, 8, 205, pp. 1-15; Published: Apr. 7, 2016.

* cited by examiner

*Primary Examiner* — Vera Afremova
(74) *Attorney, Agent, or Firm* — Chun-Ming Shih (57) ABSTRACT

The present invention is directed to a use of anti-fatigue probiotic bacteria for improving exercise performance, particularly the fatigue caused by exercise. The anti-fatigue probiotic bacteria increases muscle mass and endurance, decreases blood lactate, ammonia, and creatine kinase concentration, and changes body composition; the said bacteria can be used to improve exercise performance.

12 Claims, 6 Drawing Sheets

USE OF *LACTOBACILLUS PLANTARUM* COMPOSITION FOR MANUFACTURING ANTI-FATIGUE PROBIOTIC COMPOSITION TO IMPROVE EXERCISE PERFORMANCE

BACKGROUND OF THE INVENTION

1. Field of the Invention

The present invention relates to use of *Lactobacillus plantarum* composition for manufacturing anti-fatigue probiotic composition, in particular to reduce exercise fatigue and improve exercise performance.

2. Description of the Prior Art

*Lactobacillus plantarum* is a gram-positive bacterium that can be found in fermented food or animal's saliva. It has the largest genome in lactic acid bacteria. Therefore, *Lactobacillus plantarum* has many variations and so has many applications.

Previously studies reported that *Lactobacillus plantarum* has many medical applications, including regulation of inflammation-related diseases, protection of viral infection in respiratory tracts, reduction of accumulation in fatty liver, and increasing the sensitivity of cancer cells to the medicine mixed with *Lactobacillus plantarum*. In addition, *Lactobacillus plantarum* can be used for a variety of food additives. For example, it can be used to prevent the growth of poisonous fungi for corns.

Physiologic fatigue can be classified as muscle fatigue, chronic fatigue syndrome, and central nervous fatigue. The muscle fatigue can be caused by a large amount of exercise, resulting in motor function reduction, muscle contractility reduction, and exercise nerve retardation.

However, the study of the fatigue has its difficulties, because the fatigue is a complex physiological interaction and responses of human body structures. Thus, how to reduce fatigue is also the goal of the researchers in this field to accomplish.

Regarding the myriad of factors that can cause fatigue, creatine is an important physiological factor. The role of creatine kinase is to catalyze creatine and phosphocreatine conversion between each other, and to release ATP to provide energy during exercise. It is largely caused by skeletal muscle or myocardial exercise, but low probability caused by smooth muscle. The main reason that the concentration of creatine kinase in blood changes is exercise. After exercising, the release of creatine kinase into blood will increase for up to a week. A high concentration of creatine kinase may be a sign of muscle cell damage. The associated diseases include rhabdomyolysis, myocardial infarction, myositis, or myocarditis.

The creatinine concentration decreasing in blood usually does not have any clinical significance, but it may reflect a low amount of muscle exercise or sedentary work and lifestyle. Resting in bed will lead to decrease activity of CK more than 20%. Supplementation of creatine has long been recognized as a viable option for treatment of muscular, neurogenic or neuromuscular disorders, including arthritis, chronic congestive heart failure, wasted atrophy, ring atrophy, muscle phosphorylase deficiency, Huntington's disease, neuromuscular disorders, mitochondrial disorders, muscular dystrophy, and neuroprotection.

So far, there are a number of prior arts disclose pharmaceutical compositions to reduce the fatigue. TW I394574 discloses *Antrodia* extract can increase the metabolism of ammonia in blood to achieve the effect of slowing down fatigue. TW I465235 discloses sesame and its derivatives can enhance endurance of muscle and reduce fatigue. TW201244647 discloses the specific strain of lactic acid bacteria can be used to improve the quality of life and revitalization. In addition, U.S. Pat. No. 9,198,453 discloses administering flavanol can reduce blood lactate concentration and fatigue. U.S. Pat. No. 9,119,416 discloses alanyl-glutamine can reduce muscle fatigue and restore vitality. U.S. Pat. No. 9,023,816 discloses the extraction of *Ribes rubrum* can inhibit inflammation and muscle and enhance functions of mitochondria.

SUMMARY OF THE INVENTION

The present invention provides a method for improving exercise performance and reducing muscle fatigue comprising administering a therapeutically effective amount of a composition including *Lactobacillus plantarum* LP10 with the deposition number CGMCC13008.

In order to achieve the aforementioned objective, the reduced muscle fatigue increases the muscle mass and muscle endurance.

In order to achieve the aforementioned objective, the muscle mass is the quantity of type I muscle fibers.

In order to achieve the aforementioned objective, the increased muscle endurance improves body composition and energy use.

In order to achieve the aforementioned objective, the reduced muscle fatigue reduces the release of creatine kinase from muscle cells.

In order to achieve the aforementioned objects, the reduced muscle fatigue reduces the concentration of serum lactate and serum ammonia.

In order to achieve the aforementioned objective, the muscle fatigue is caused by skeletal muscle disease or skeletal muscle abnormality.

In order to achieve the aforementioned objective, the reduced muscle fatigue is caused by long-term exercise or high-intensive exercise.

In order to achieve the aforementioned objective, wherein the *Lactobacillus plantarum* LP10 is selective from the group consisting of live *Lactobacillus plantarum* LP10 and dead *Lactobacillus plantarum* LP10.

In order to achieve the aforementioned objective, wherein the composition is in a dosage form suitable for oral administration.

In order to achieve the aforementioned objective, wherein the dosage form is selected from the group consisting of solutions, suspensions, emulsions, powders, tablets, pills, syrups, lozenges, troches, chewing gums, slurries and capsules.

In order to achieve the aforementioned objective, wherein the composition further comprises an edible material, the edible material comprises water, fluid milk product, milk, concentrated milk, fermented milk, sour milk, frozen yogurt, lactic acid bacterial-fermented beverages, milk powder, ice cream, cream cheese, dry cheese, soybean milk, fermented soybean milk, vegetable-fruit juice, fruit juice, sports drinks, confectioneries, jellies, candies, infant formulas, health foods, animal feeds, Chinese herbs or dietary supplements.

In order to achieve the aforementioned objective, wherein the composition further comprises at least one of the probiotic bacteria strain selected from the group consisting of

*Lactobacillus* sp., *Streptococcus* sp., *Bifidobacterium* sp., *Saccharomyces* sp. and yeasts.

DETAILED DESCRIPTION OF THE PREFERRED EMBODIMENT

The technical features of the present invention, including specific features, are defined by the claims. For the technical features of the present invention, the understanding, preferably, should coordinate with the specification, the embodiment, the drawings and the detailed description.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

As used herein, the term "probiotics" refers to microorganisms that provide a physiological benefit to a user when given properly. The microorganisms have no toxicity, but intestinal adhesion and beneficial effects.

The term "carrier" or "vehicle" as used herein, refers to relatively nontoxic chemical compounds or agents that facilitate the incorporation of a compound into cells or tissues.

The foregoing may be aromatics, buffers, binders, colorants, disintegrants, diluents, emulsifiers, extenders, flavor-improving agents, gellants, glidants, antiseptics, skin-penetration enhancers, solubilizers, stabilizers, suspending agents, sweeteners, tonicity agents, viscosity-increasing agents, or any combination thereof.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "combination" as used herein, means a product that results from the mixing or combining of more than one active ingredient and includes both fixed and non-fixed combinations of the active ingredients. The term "fixed combination" means that the active ingredients, e.g. an anti-cancer agent encapsulated in nanoparticles described herein and a co-agent, are both administered to a patient simultaneously in the form of a single entity or dosage. The term "non-fixed combination" means that the active ingredients, e.g. an anti-cancer agent encapsulated in nanoparticles described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "fatigue" as used herein, include muscle fatigue caused by prolonged exercise, muscle fatigue caused by high-intensity exercise, muscle fatigue caused by long-term stress, muscle caused by high-intensity exercise in an individual fatigue, age-related muscle fatigue in an individual is associated with muscle fatigue due to disease or abnormalities, muscle fatigue caused by myopathy, or muscle fatigue due to muscle atrophy of the individual.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

The appropriate routes of administration include, but not limited to, oral, intravenous, rectal, aerosol, parenteral, ocular, pulmonary, mucosal penetration through the skin, vaginal, otic, nasal, and topical.

In addition, examples of gastrointestinal administration include, but not limited to, intramuscular, subcutaneous, intravenous, intramedullary, and intramedullary, intraventricular, intraperitoneal, intra-lymph, intranasal.

The following treatment embodiments are illustrative only, due to the large variability of individual treatment sessions, and the deviation from the recommended value is not unusual. The dose may vary, depending on the variation, but not limited to the activity of the compound, the disease or physiological state of treatment, the mode of administration, individual needs, severity of the disease, and physician judgment.

The toxicity and efficacy of the treatment may be determined by standard pharmaceutical procedures for cell culture or animal testing, including but not limited to, determining the effective dose ($ED_{50}$, half the dose of therapeutic effect).

The probiotic combination used in the present invention, herein the probiotic may be active or inactive. Furthermore, the inactive probiotic can be heat inactivation or lyophilization.

The probiotic combination herein include, but not limited to, solutions, emulsions, suspensions, powders, tablets, pills, Lozenge, troche, chewing gum, capsules, and other dosage forms similar or applicable to the present invention.

The probiotic combination herein may optionally include other strains as taught by a person having ordinary skill in the art.

The inventive composition may further include at least one of the following groups of known probiotic strains: *Lactobacillus* sp., *Streptococcus* sp., *Bifidobacterium* sp., and yeasts.

Furthermore, the known *Lactobacillus* sp. include, but are not limited to, *Lactobacillus lactis*, *Lactobacillus acidophilus*, *Lactobacillus helveticus*, *Lactobacillus bifidus*, *Lactobacillus casei*, *Lactobacillus paracasei* subsp. *paracasei*, *Lactobacillus rhamnosus*, *Lactobacillus gasseri*, *Lactobacillus reuteri* and *Lactobacillus fermentum* or their combinations thereof.

The known *Streptococcus* sp. include, but are not limited to, *Streptococcus lactis*, *Streptococcus thermophilus*, *Streptococcus cremoris* or their combinations thereof.

The known *Bifidobacterium* sp. include, but are not limited to, *Bifidobacterium breve*, *Bifidobacterium lactis*, *Bifidobacterium longum*, *Bifidobacterium bifidum* or their combinations thereof.

The known yeasts include, but are not limited to, *Saccharomyces cereviseae*, *Candida kefyr*, *Saccharomyces florentinus* or their combinations thereof.

The probiotic combination herein may be a food composition, further formulate as a capsule, lozenge, beverage, powder, or dairy product, optionally, other probiotics such as *Enterococcus*, *Bifidobacterium*, *Bacillus*, *Streptococcus* and *Lactococcus*.

The composition provided herein can be manufactured as a food product or health product by addition of an edible material. Said edible material includes, but is not limited to, water, fluid milk products, milk, concentrated milk, fermented milk, yogurt, sour milk, frozen yogurt, lactic acid bacteria-fermented beverages, milk powder, ice cream, cream cheese, dry cheese, soybean milk, fermented soybean milk, vegetable-fruit juices, juices, sports drinks, confectioneries, jellies, candies, infant formulas, health foods, animal feeds, Chinese herbs and dietary supplements.

The composition provided herein can be manufactured as a dietary supplements which may be administered to a user in admixture with a suitable drinkable liquid such as water, yoghurt, milk or fruit juice or may be mixed with a solid or liquid food product. The excipient included in the inventive composition consists of, but is not limited to, solution, suspension, emulsion, powder, tablet, pill, lozenge, troche, chewing gum, slurry and other similar or suitable dosage forms for use in the invention.

In general, the combinations described in this specification, as well as other pharmaceutical ingredients, need not to be administered in the same pharmaceutical combination. In the embodiment, it can be administered via different routes due to different physical and chemical properties. In the present embodiment, the initial administration route can be changed according to the established administration procedure, and then further changed depending on the clinical drug efficacy, dosage, administration mode, administration frequency.

In the present embodiment of the invention, the therapeutically effective dose varies depending on the combination therapy. The combination therapy may further include a periodical treatment, referring to multiple initiation and cessation of treatments to assist in the clinical management of the patient. The description in the present specification regarding the combination treatment and the dose of co-administration are varied by the co-administered drug, the disease, the physiological abnormality, and the physiological condition.

In the present embodiment of the invention, in order to achieve the treatment, prevention, or amelioration of physiological conditions and symptoms, medication administration is based on a number of factors to change or amend. The aforementioned factors include physiological abnormalities of patients, age, weight, sex, diet, drug usage. Therefore, in another embodiment, the dose of treatment can be widely changed and deviated from the first course of treatment.

*Lactobacillus plantarum* TWK10 strain (also named as *Lactobacillus plantarum* LP10) has been deposited in China General Microbiological Culture Collection Center (CG-MCC) with deposit number CGMCC No. 13008, on Sep. 13, 2016, also deposited at Bioresource Collection and Research Center of Taiwan with deposit number BCRC No. 910734, on Jun. 30, 2016. Before testing, the bacterial strains were retrieved from frozen storage and cultured in MRS broth for 24 h at 37° C. Before supplementation, cells were centrifuged at 3000 g for 10 min and washed twice with phosphate buffered saline (PBS). Pellets were resuspended in PBS, pH 7.2.

Male ICR mice (6 weeks old) grown under specific pathogen-free conditions were purchased from BioLASCO (Yi-Lan, Taiwan). All mice were provided a standard laboratory diet (No. 5001; PMI Nutrition International, Brentwood, Mo., USA) and distilled water ad libitum and housed at 12-h light/12-h dark cycle at room temperature (22° C.±1° C.) and 50%-60% humidity.

All data are expressed as mean±SEM, n=8 mice/group. Statistical differences among groups were analyzed by a one-way analysis of variance (ANOVA) and the Cochran-Armitage test for the dose-effect trend analysis with SAS 9.0 (SAS Inst., Cary, N.C., USA). $p<0.05$ was considered statistically significant. Differences between groups were analyzed by one-way ANOVA using Duncan's post-hoc test, and p values <0.05 were considered significant.

Example 1 Effect of LP10 on Exercise Performance Test

The human dose of LP10, $1 \times 10^{10}$ CFU per day, was modified from previous studies. The mouse LP10 dose ($2.05 \times 10^8$ CFU/kg) we used was converted from a human equivalent dose (HED) based on body surface area by the following formula from the US Food and Drug Administration: assuming a human weight of 60 kg, the HED for $1 \times 10^{10}$ colony-forming units (CFU)÷60 (kg)=$16.67 \times 10^7 \times 12.3$=a mouse dose of $2.05 \times 10^8$ CFU/kg; the conversion coefficient 12.3 was used to account for differences in body surface area between a mouse and a human.

In total, 24 mice were randomly assigned to 3 groups (8 mice/group) for daily oral LP10 treatment for 6 weeks: vehicle, $2.05 \times 10^8$ CFU/kg (LP10-1X), and $1.03 \times 10^9$ CFU/kg (LP10-5X). The vehicle group received the same volume of solution equivalent to individual body weight (BW). After supplement for six weeks, a low-force testing system (Model-RX-5, Aikoh Engineering, Nagoya, Japan) was used to measure the forelimb grip strength of treated mice.

Figure 1:
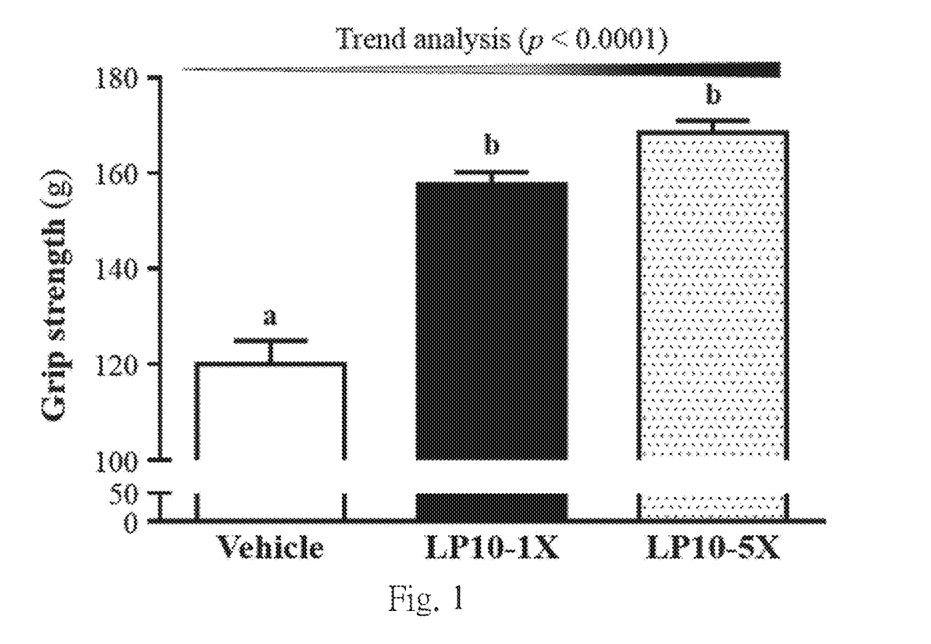
FIG. 1 shows the effect of LP10 supplementation for six weeks on forelimb grip strength.

Mice were pretreated with vehicle, LP10-1X, or LP10-5X for six weeks, and then forelimb grip strength was tested. Data are mean±SEM, 8 mice/group, by one-way ANOVA. Different letters (a, b) indicate a significant difference at p<0.05. The forelimb grip strengths in the vehicle, LP10-1X, and LP10-5X groups were 120±5, 158±3, and 168±3 g, respectively (FIG. 1). Forelimb grip strengths were 1.31 and 1.40 fold higher in the LP10-1X and LP10-5X groups than in the vehicle treatment group (both p<0.0001). In the trend analysis, absolute forelimb grip strength dose-dependently increased with increasing LP10 dose (p<0.0001).

In general, programmed exercise training is required to increase grip strength; however, we found that LP10 supplementation benefited grip strength even though test animals did not undergo a training intervention. Thus, long-term LP10 supplementation could benefit the muscle explosive force when no training protocol is implemented. Thus, LP10 could increase in muscle mass and forelimb grip strength.

The swim-to-exhaustion test is used to examine exercise performance ability. The swim-to-exhaustion test involved loads corresponding to 5% of the mouse BW attached to the tail to evaluate endurance time. The swimming endurance time of each mouse was recorded from beginning to exhaustion, determined by observing loss of coordinated movements and failure to return to the surface within 7 seconds.

Figure 2:
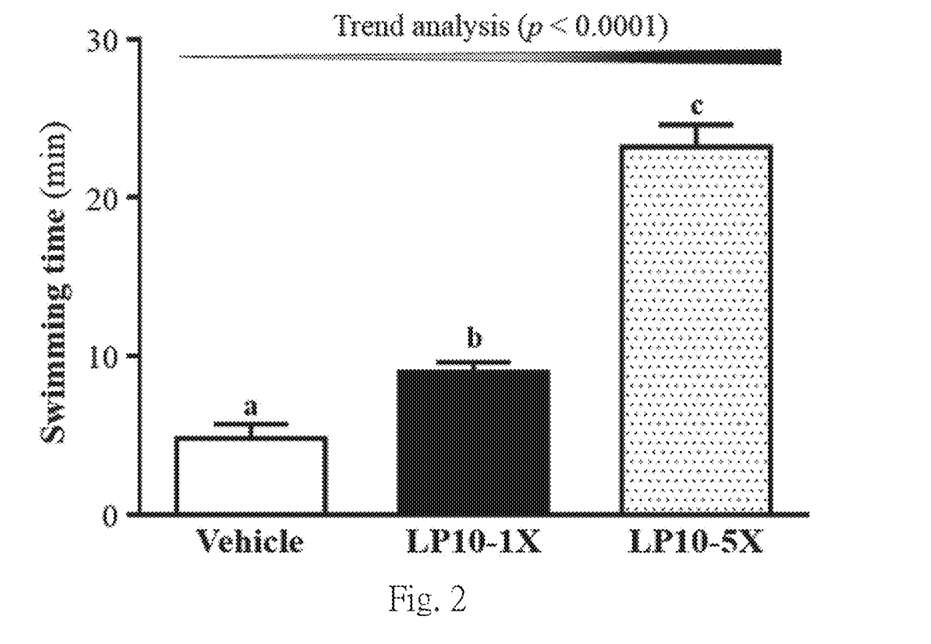
FIG. 2 shows the effect of LP10 supplementation on swimming exercise performance.

Energy metabolism during muscular activity determines the level of physiological fatigue. An important index in evaluating anti-fatigue treatment is exercise endurance. Mice were pretreated with vehicle, LP10-1X, LP10-5X for six weeks, and then performed an exhaustive swimming exercise with a load equivalent to 5% of body weight attached to the tail. Data are mean±SEM, n=8 mice/group, by one-way ANOVA. Different letters (a, b) indicate a significant difference at p<0.05. Endurance swimming times were 4.8±0.9, 9.0±0.6, and 23.2±1.4 min with vehicle, LP10-1X, and LP10-5X treatment, respectively (FIG. 2). The exhaustive swimming time was longer, by 1.85 (p=0.0183) and 4.81 folds (p<0.0001), with LP-1X and LP-5X, respectively, than with vehicle treatment. In the trend analysis, endurance swimming time dose-dependently increased with increasing LP10 dose (p<0.0001). LP10 may improve endurance performance in the absence of training.

Example 2 Effect of LP10 Supplementation on Serum Lactate, Ammonia, Glucose, CK and BUN Levels after Acute Exercise Challenge Exercise-induced muscle fatigue can be evaluated by biochemical indicators such as lactate, ammonia, glucose, CK, and BUN levels. Lactate accumulates in the blood and in the muscles engaged in the exercise and exceeds the aerobic metabolic capacity. When the lactic acid concentration increases, hydrogen ions accumulate, which leads to fatigue due to acidification.

The effect of LP10 supplementation on fatigue-associated biochemical indices was evaluated after exercise. At 1 h after LP10 supplementation, all mice underwent a 15-min swim test without weight loading. After a 15-min swim exercise, blood samples were immediately collected and centrifuged at 1500× g and 4° C. for 10 min for serum separation. Serum lactate, ammonia, glucose, creatine kinase (CK) and blood urea nitrogen (BUN) levels were determined using the Beckman DxC 800 autoanalyzer (Beckman Coulter, Brea, Calif., USA).

Figure 3:
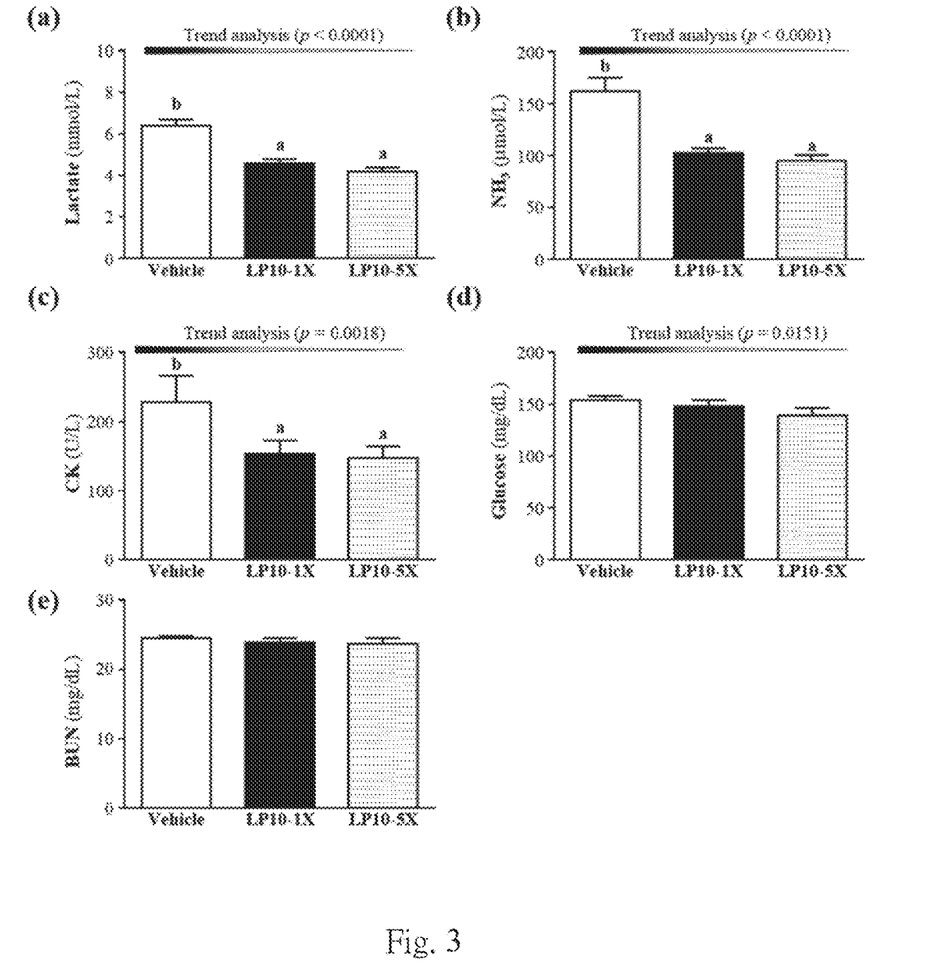
FIG. 3 shows the effect of LP10 supplementation on serum levels of lactate, ammonia, creatine kinase (CK), glucose, and blood urea nitrogen (BUN) after acute exercise challenge.

Lactate levels in the vehicle, LP10-1X, and LP-5X groups were 6.4±0.3, 4.6±0.2, and 4.2±0.7 mmol/L, with lower lactate levels with LP10-1X and LP10-5X supplementation (27.88%, p=0.0004 and 34.11%, p=0.0005, respectively) than with vehicle treatment (FIG. 3A). In the trend analysis, serum lactate level was dose-dependently decreased with increasing LP10 dose (p<0.0001). LP10 supplementation may have potential for the removal and utilization of blood lactate after exercise.

Ammonia, another important metabolite produced during energy metabolism for exercise, is generated by different sources. Accumulation of ammonia in the blood and brain during exercise can negatively affect the central nervous system and cause fatigue.

Serum ammonia levels were 162.1±13, 102.5±4.3, and 95±5.5 μmol/L in the vehicle, LP10-1X, and LP10-5X groups, respectively (FIG. 3B), and levels were lower, by 36.78% (p=0.0004) and 41.40% (p=0.0001), with LP10-1X and LP10-5X, respectively, than with vehicle treatment. Trend analysis showed that the serum ammonia level dose-dependently decreased with increasing LP10 dose (p<0.0001). Thus, continuous supplementation with LP10 for six weeks could decrease ammonia levels during exercise.

The blood glucose level is an important index for performance maintenance during exercise. The serum glucose levels were 154.1±4, 148.3±6, and 139±7 mg/dL in the vehicle, LP10-1X, and LP10-5X groups, respectively, with no difference among groups (FIG. 3D). Trend analysis showed that serum glucose levels dose-dependently decreased with increasing LP10 dose (p=0.0151). Therefore, continuous supplementation with LP10 for six weeks could increase energy utilization and improve exercise performance.

Serum CK level is an important clinical biomarker of muscle damage, muscular dystrophy, severe muscle breakdown, myocardial infarction, autoimmune myositides, and acute renal failure. We found serum CK levels of 228.3±38.4, 154.1±18.8, and 147.8±16.5 mg/dL in the vehicle, LP10-1X, and LP10-5X groups, respectively (FIG. 3C), with lower levels with LP-1X and LP-5X, by 32.48% (p=0.0165) and 35.27% (p=0.0142), respectively, than with vehicle treatment. Trend analysis revealed that LP10 treatment had a significant dose-dependent effect on CK level (p=0.0118). Therefore, LP10 supplementation could ameliorate skeletal muscle injury induced by acute exercise challenge.

BUN is an important biochemical parameter related to fatigue. The BUN level is used to measure the amount of nitrogen in blood from the waste product of urea. Urea serves an important role in the metabolism of nitrogen-containing compounds. Consequently, an increased BUN level reflects the decomposition of protein, which will adversely affect the contractive strength of muscle and lead to fatigue. Serum BUN level did not differ among treatment groups (FIG. 3E).

Above all, LP10 may have potential as an ergogenic supplement by improving gut microbiota and regulating energy utilization. LP10 supplement decrease fatigue-associated biochemical factors.

Figure 4:
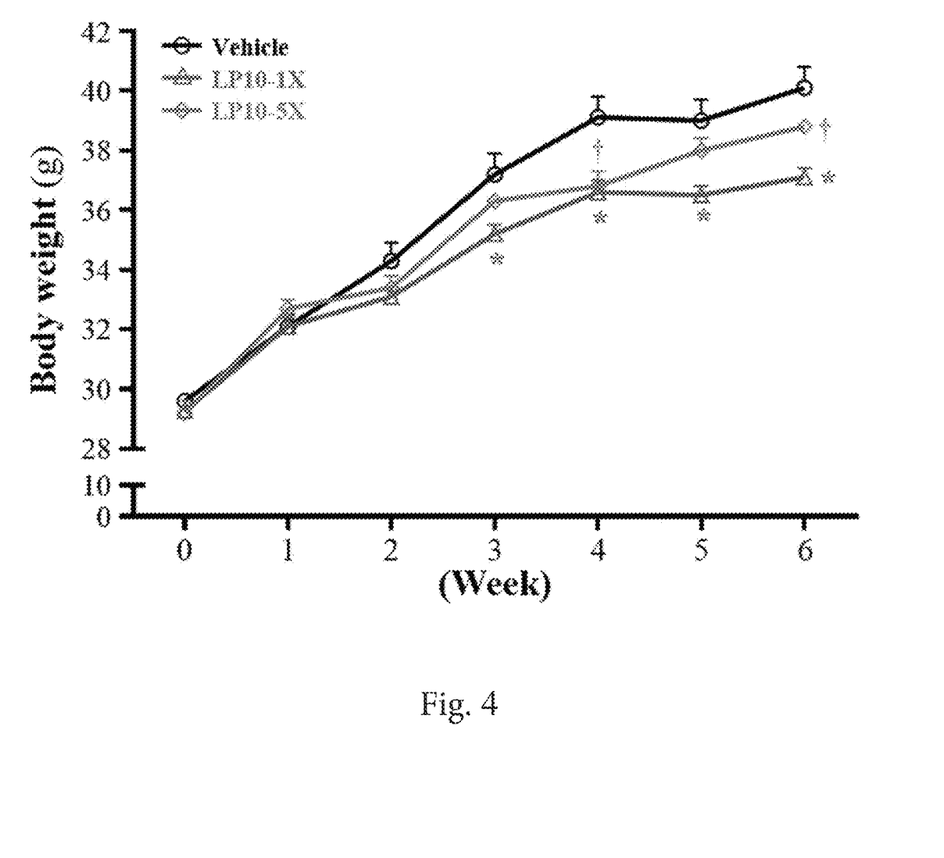
FIG. 4 shows the change in body weight (BW) during the experiment.

Example 3 General Characteristics of Mice with LP10 Supplementation for Six Weeks After LP10 supplement for six weeks, all mice were euthanized with 95% $CO_2$ asphyxiation. Initial BW did not differ among the vehicle, LP10-1X, and LP10-5X groups (Table 1). After six-week supplementation with LP10, the final BW was lower with LP10-1X and LP10-5X, by 7.47% (p=0.0003) and 3.46% (p=0.0567), respectively, than with vehicle treatment. In addition, daily intake of diet and water increased in LP10-5X fed mice. Trend analysis showed that daily intake of diet (p<0.0001) and water (p<0.0001) dose-dependently increased with LP10 supplementation, so daily diet intake was increased but BW was decreased. In addition, BW was significantly lower (p<0.05) with vehicle treatment at Week 3 of LP10 supplementation (FIG. 4). Thus, three-week LP10 supplementation may change the body composition and energy utilization.

We measured the effect of LP10 on the muscle and epididymal fat pad (EFP) mass and relative tissue weight (different tissue weights adjusted for individual BW %). The EFP weight was lower by 34.62% (p=0.003) and 50.30% (p<0.0001) with LP10-1X and LP10-5X, respectively, than with vehicle treatment. Trend analysis showed that EFP weight dose-dependently decreased with LP10 supplementation (p<0.0001). The relative weight of EFP (%) was lower by 28.93% (p=0.0048) and 48.22% (p<0.0001) with LP10-1X and LP10-5X, respectively, than with vehicle treatment.

The relative weight (%) of muscle (gastrocnemius and soleus muscles) was greater by 1.10 (p=0.0003) and 1.07 folds (p=0.0098) with LP10-1X and LP10-5X, respectively, than with vehicle treatment. Trend analysis also showed a significant dose-dependent decrease and increase in relative EFP weight (%) and relative muscle weight (%), respectively, with LP10 supplementation. Thus, supplementation of LP10 for six weeks could change body composition to more fit and stronger. In addition, trend analysis showed significant increases in relative weight (%) of the kidney (p<0.0001) and heart (p=0.0018) with increasing LP10 dose. We found no gross abnormalities attributed to LP10 when weighing organs.

TABLE 1

General characteristics of mice with LP10 supplementation.

| Characteristics | Vehicle | LP10-1X | LP10-5X | Trend analysis |
|---|---|---|---|---|
| Initial BW (g) | 29.6 ± 0.2 | 29.3 ± 0.3 | 29.2 ± 1.2 | 0.5370 |
| Final BW (g) | 40.1 ± 0.7 [c] | 37.1 ± 0.3 [a] | 38.8 ± 0.1 [a, b] | 0.6493 |
| Food intake (g/day) | 6.3 ± 0.1 [a] | 6.2 ± 0.0 [a] | 7.5 ± 0.1 [b] | <0.0001(↑) |
| Water intake (mL/day) | 6.9 ± 0.1 [a] | 6.8 ± 0.2 [a] | 7.6 ± 0.0 [b] | <0.0001(↑) |
| weight (g) | | | | |
| Liver (g) | 2.13 ± 0.05 | 2.10 ± 0.05 | 2.10 ± 0.03 | 0.9075 |
| Kidney (g) | 0.68 ± 0.02 | 0.67 ± 0.04 | 0.72 ± 0.04 | 0.1272 |
| EFP (g) | 0.85 ± 0.07 [b] | 0.55 ± 0.03 [a] | 0.42 ± 0.05 [a] | <0.0001 (↓) |
| Heart (g) | 0.20 ± 0.01 | 0.20 ± 0.01 | 0.20 ± 0.00 | 0.3908 |
| Lung (g) | 0.21 ± 0.01 | 0.22 ± 0.01 | 0.21 ± 0.00 | 0.9353 |
| Muscle (g) | 0.36 ± 0.01 | 0.37 ± 0.01 | 0.37 ± 0.01 | 0.4790 |
| BAT (g) | 0.13 ± 0.01 | 0.12 ± 0.00 | 0.13 ± 0.01 | 0.9473 |
| Relative weight (%) | | | | |
| Liver | 5.29 ± 0.03 [a] | 5.65 ± 0.09 [b] | 5.43 ± 0.06 [a] | 0.1073 |
| Kidney | 1.70 ± 0.02 [a] | 1.81 ± 0.02 [b] | 1.86 ± 0.03 [b] | <0.0001 (↑) |
| EFP | 2.09 ± 0.16 [c] | 1.48 ± 0.09 [b] | 1.08 ± 0.15 [a] | <0.0001 (↓) |
| Heart | 0.49 ± 0.10 [a] | 0.54 ± 0.07 [b] | 0.53 ± 0.07 [b] | 0.0018 (↑) |
| Lung | 0.53 ± 0.03 [a] | 0.58 ± 0.03 [b] | 0.55 ± 0.01 [ab] | 0.2009 |
| Muscle | 0.90 ± 0.02 [a] | 0.99 ± 0.01 [b] | 0.96 ± 0.02 [b] | 0.0326 (↑) |
| BAT | 0.31 ± 0.01 | 0.31 ± 0.01 | 0.33 ± 0.02 | 0.6881 |

Data are mean ± SEM, n = 8 mice/group. Different letters (a, b, c) in the same row indicate a significant difference at p < 0.05. Food efficiency ratio: body weight (BW) gain (g/day)/food intake (g/day). Muscle mass includes both gastrocnemius and soleus muscles in the back part of the lower legs. BAT: brown adipose tissue; EFP: epididymal fat pad. Mice were pretreated with vehicle, LP10-1X, or LP10-5X for six weeks.

Example 4 Effect of LP10 Supplementation on Biochemical Variables at the End of the Experiment We further investigated whether six-week LP10 treatment affected other biochemical markers in healthy mice. We examined tissue- and health status-related biochemical variables and major organs including skeletal muscle, heart, kidney, and lung (Table 2).

TABLE 2

Biochemical analysis with LP10 supplementation at the end of the experiment.

| Variable | Vehicle | LP10-1X | LP10-5X | Trend Analysis |
|---|---|---|---|---|
| CK (U/L) | 193 ± 36 | 169 ± 22 | 181 ± 25 | 0.8469 |
| TP (g/dL) | 4.8 ± 0.1 | 4.9 ± 0.1 | 4.9 ± 0.1 | 0.9571 |
| Albumin(g/dL) | 3.6 ± 0.0 $^b$ | 3.6 ± 0.0 $^b$ | 3.3 ± 0.1 $^a$ | 0.012(↓) |
| BUN(mg/dL) | 26.5 ± 0.5 $^b$ | 22.4 ± 0.6 $^a$ | 23.0 ± 0.9 $^a$ | 0.0017(↓) |
| Creatinine (mg/dL) | 0.27 ± 0.01 | 0.27 ± 0.01 | 0.29 ± 0.01 | 0.4627 |
| UA(mg/dL) | 0.91 ± 0.03 | 1.01 ± 0.10 | 1.03 ± 0.10 | 0.5858 |
| TC(mg/dL) | 143 ± 6 | 144 ± 6 | 130 ± 3 | 0.1804 |
| TG(mg/dL) | 205 ± 12 $^b$ | 159 ± 11 $^a$ | 151 ± 6 $^a$ | 0.0005 |
| Glucose (mg/dL) | 166 ± 4 | 161 ± 5 | 157 ± 5 | 0.1336 |

Data are mean ± SEM, n = 8 mice/group. Different letters (a, b) in the same row indicate a significant difference at p < 0.05 by one-way ANOVA. CK, creatine kinase; TP, total protein; BUN, blood urea nitrogen; UA, uric acid; TC, total cholesterol; TG, triacylglycerols.

Levels of biochemical indices, including CK, TP, creatinine, UA, TC, and glucose, did not differ among groups (p>0.05, Table 2). Serum albumin levels were lower by 7.64% (p=0.0375) with LP10-5X than with vehicle treatment. Serum BUN levels were lower by 15.50% (p=0.0218) and 13.29% (p=0.0037) with LP10-1X and LP10-5X, respectively, than with vehicle treatment. On trend analysis, serum albumin (p=0.0012) and BUN (p=0.0017) levels were dose-dependently decreased with LP10 supplementation. Therefore, long-term daily supplementation with LP10 may have potential for tissue protection and renal benefits.

In addition, serum level of TC, an index of lipid profile, was lower by 22.76% (p=0.0069) and 26.60% (p=0.0021) with LP10-1X and LP10-5X, respectively, than with vehicle treatment. Trend analysis showed significantly decreased serum TG levels (p=0.0005) with increasing LP10 dose.

Figure 5:
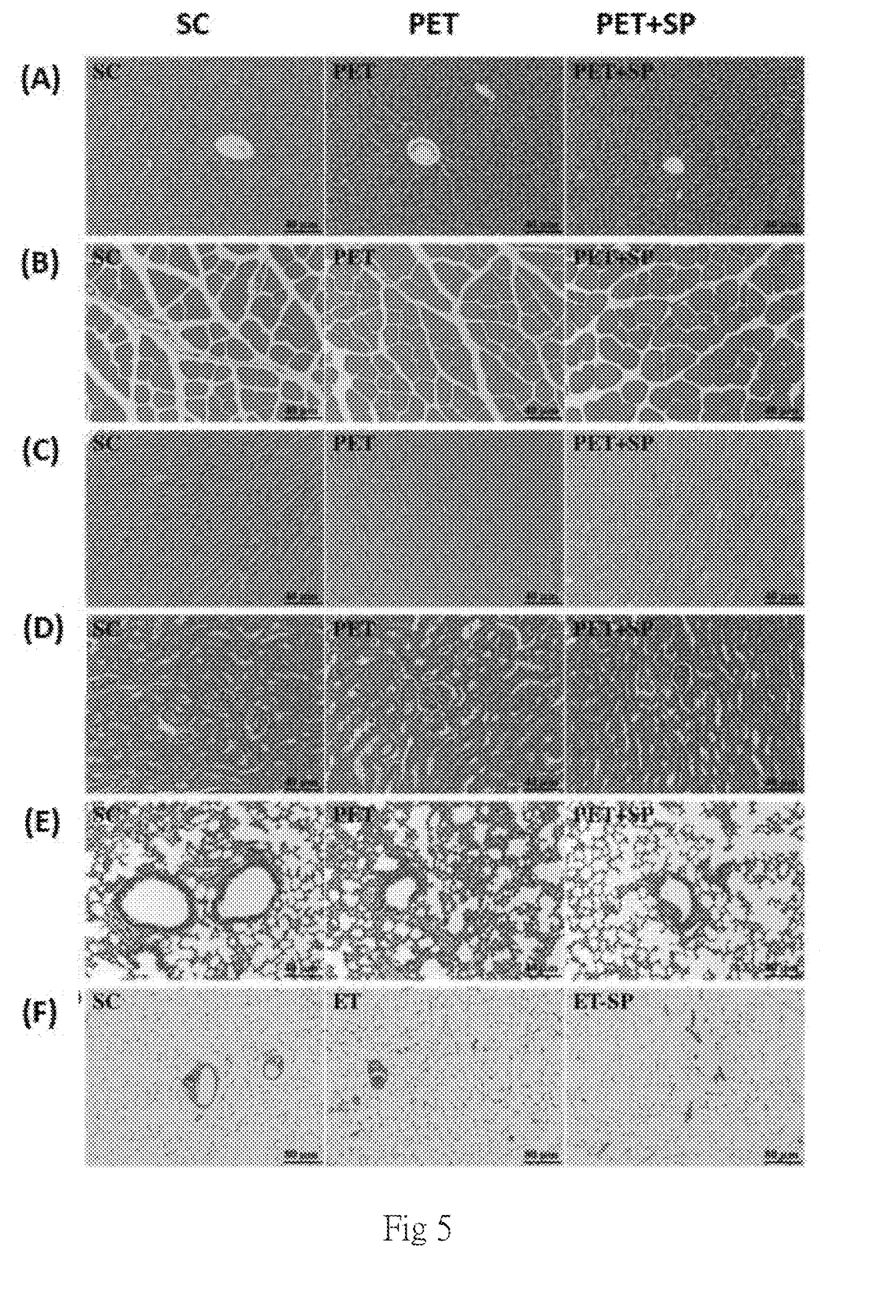
FIG. 5 shows the effect of LP10 supplementation on morphology of: liver, skeletal muscle, heart, kidney, lungs, and epididymal fat pad.

All tissues were carefully removed, minced, and fixed in 10% formalin after sacrifice. Samples were embedded in paraffin and cut into 4-μm thick slices for morphological and pathological evaluations. Tissue was stained with hematoxylin and eosin (H & E) and examined under a light microscope equipped with a CCD camera (BX-51, Olympus, Tokyo, Japan) by a veterinary pathologist. LP10 supplementation for six weeks had no adverse effects on major organs such as the liver (FIG. 5a), skeletal muscle (FIG. 5b), heart (FIG. 5c), kidney (FIG. 5d), lung (FIG. 5e), and EFP (epididymal fat pad, FIG. 5f). Therefore, the dose of LP10 supplementation used in this study was safe.

Example 5 IHC of Gastrocnemius Muscles for Type I and Type II Muscle Fibers

Target organs were carefully removed, minced, and fixed in 10% formalin after sacrifice. Tissues were embedded in paraffin and cut into 4-μm thick slices for morphological and pathological evaluations. Immunohistochemical (IHC) staining of tissues involved use of the Leica antibody to myosin heavy chain fast (WB-MHCf) and myosin heavy chain slow (WB-MHCs). By using automated BondMax with double staining, WB-MHCf and WB-MHCs epitope retrieval involved use of ER2 (AR9640) (pH 9) retrieval solution for 30 min once, followed by incubation with WB-MHCf and WB-MHCs antibodies at a 100-fold dilution for 30 min. The detection kit used was the Bond Polymer Refine Detection (DS9800) (incubation with post primary for 8 min, polymer for 8 min and 3',3'-diaminobenzidine for 5 min) and Bond Polymer Refine Red Detection (DS9390) (incubation with post primary for 20 min, polymer for 30 min, Red for 10 min and haematoxylin for 5 min). Finally, results were examined under a light microscope equipped with a CCD camera (BX-51, Olympus, Tokyo) by a veterinary pathologist.

Figure 6:
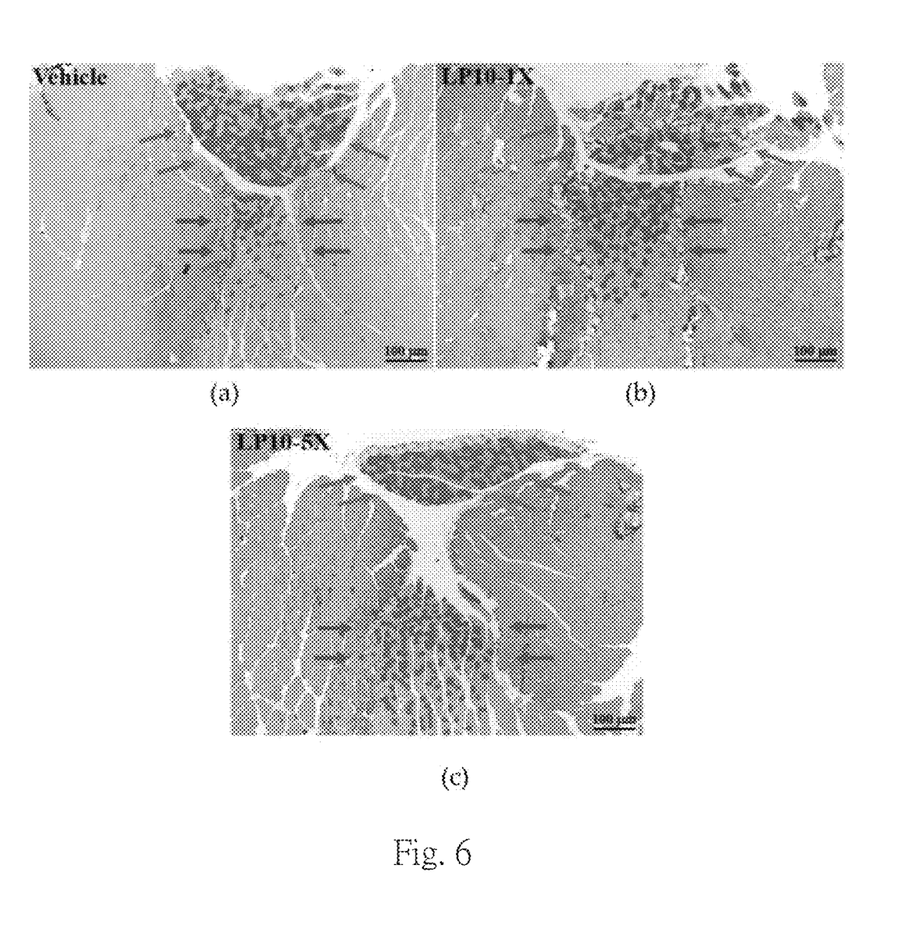
FIG. 6 shows of effect of LP10 supplementation on type I and type II muscle fibers in gastrocnemius muscle.
Figure 7:
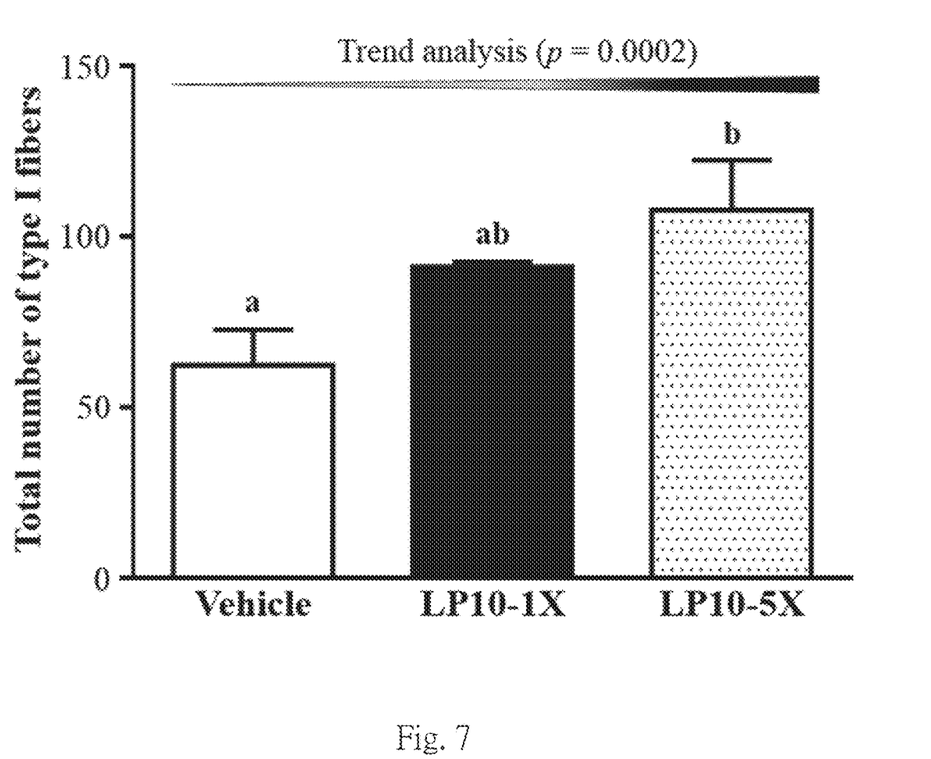
FIG. 7 shows total number of type I muscle fibers with LP10 supplementation in gastrocnemius muscle of mice.

IHC showed slow muscle as type I fibers and fast muscle as type II fibers in gastrocnemius muscle of treated mice (FIG. 6). Data are mean±SEM, n=8 mice/group. Different letters (a, b) indicate a significant difference at p<0.05 by one-way ANOVA. The number of Type I muscle fibers (red arrow) were increased significantly with LP10 treatment than with vehicle treatment. The numbers of type I muscle fibers were 62±10, 91±2, and 108±15 with vehicle, LP10-1X, and LP10-5X treatment, respectively (FIG. 7), and was higher, by 1.72 folds (p=0.0223), with LP10-5X than with vehicle treatment. Trend analysis revealed that LP10 treatment dose-dependently affected the type I muscle fiber. Therefore, LP10 supplementation could increase type I muscle fiber in gastrocnemius muscle to promote exercise endurance.

The above-mentioned detailed description aims to specifically illustrate the practicable embodiments of the present invention, but the embodiments are not for limiting the patent scope of the present invention and all equivalent embodiments or modifications made without departing from the spirit of the present invention shall be contained within the patent scope of the present invention.

The plentiful effects above-mentioned meet the lawful patent requirement for novelty and inventiveness. The inventor files an application according to law and earnestly urge honorable Office to approve the patent application of the present invention as an encouragement thereof.

What is claimed is:

1. A method for improving exercise performance and reducing muscle fatigue, comprising
   administering a therapeutically effective amount of a composition including *Lactobacillus plantarum* LP10 with the deposition number CGMCC13008;
   wherein reducing muscle fatigue includes increasing muscle mass and muscle endurance; and
   wherein the therapeutically effective amount is at least $10^{10}$ CFU per day.

2. The method of claim 1, wherein the muscle mass is the quantity of type I muscle fibers.

3. The method of claim 1, wherein the increasing muscle endurance comprises improving body composition and energy use.

4. The method of claim 1, wherein the reducing muscle fatigue comprises reducing release of creatine kinase from muscle cells.

5. The method of claim 1, wherein the reducing muscle fatigue comprises reducing serum lactate and serum ammonia.

6. The method of claim 1, wherein the muscle fatigue is caused by skeletal muscle disease or skeletal muscle abnormality.

7. The method of claim 1, wherein the muscle fatigue is caused by long-term exercise or high-intensive exercise.

8. The method of claim 1, wherein the *Lactobacillus plantarum* LP10 is selective from the group consisting of live *Lactobacillus plantarum* LP10 and dead *Lactobacillus plantarum* LP10.

9. The method of claim 1, wherein the composition is in a dosage form suitable for oral administration.

10. The method of claim 9, wherein the dosage form is selected from the group consisting of solutions, suspensions, emulsions, powders, tablets, pills, syrups, lozenges, troches, chewing gums, slurries and capsules.

11. The method of claim 1, wherein the composition further comprises an edible material, the edible material comprises water, fluid milk product, milk, concentrated milk, fermented milk, sour milk, frozen yogurt, lactic acid bacterial-fermented beverages, milk powder, ice cream, cream cheese, dry cheese, soybean milk, fermented soybean milk, vegetable-fruit juice, fruit juice, sports drinks, confectioneries, jellies, candies, infant formulas, health foods, animal feeds, Chinese herbs or dietary supplements.

12. The method of claim 1, wherein the composition further comprises at least one of the probiotic bacteria strain selected from the group consisting of *Lactobacillus* sp., *Streptococcus* sp., *Bifidobacterium* sp., *Saccharomyces* sp. and yeasts.

\* \* \* \* \*